US012797569B2

(12) United States Patent
Baba et al.

(10) Patent No.: US 12,797,569 B2
(45) Date of Patent: Nov. 17, 2026

(54) MASK

(71) Applicant: NIHON KOHDEN CORPORATION, Tokyo (JP)

(72) Inventors: Yuya Baba, Tokorozawa (JP); Takayuki Aoyagi, Tokorozawa (JP); Isao Matsubara, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 955 days.

(21) Appl. No.: 17/653,345

(22) Filed: Mar. 3, 2022

(65) Prior Publication Data

US 2022/0288339 A1 Sep. 15, 2022

(30) Foreign Application Priority Data

Mar. 12, 2021 (JP) ................................ 2021-040786

(51) Int. Cl.
*A61M 16/06* (2006.01)

(52) U.S. Cl.
CPC .... *A61M 16/0622* (2014.02); *A61M 16/0683* (2013.01)

(58) Field of Classification Search
CPC .. A61M 16/00; A61M 16/06; A61M 16/0616; A61M 16/0622; A61M 16/0683; A61M 2202/0225; A61M 2206/20; A61M 2230/43
USPC .................................................... 128/206.24
See application file for complete search history.

(56) References Cited

U.S. PATENT DOCUMENTS

| | | | | |
|---|---|---|---|---|
| 4,574,799 | A * | 3/1986 | Warncke | A62B 18/02 128/207.12 |
| 4,895,172 | A * | 1/1990 | Lindkvist | A61M 16/009 128/863 |
| 6,530,373 | B1 | 3/2003 | Patron et al. | |
| 8,136,524 | B2 | 3/2012 | Ging et al. | |
| 8,146,595 | B2 | 4/2012 | Sherman | |
| 10,384,027 | B2 | 8/2019 | Harrison | |
| 10,653,854 | B2 | 5/2020 | Prentice et al. | |
| 11,344,753 | B2 * | 5/2022 | Wang | A62B 18/10 |

(Continued)

FOREIGN PATENT DOCUMENTS

| | | | |
|---|---|---|---|
| CN | 107198274 | A * | 9/2017 |
| JP | 2007516749 | A | 6/2007 |

(Continued)

OTHER PUBLICATIONS

Wan, English Translation of "CN-107198274-A", Sep. 26, 2017 (Year: 2017).*

(Continued)

*Primary Examiner* — Rachel T Sippel
*Assistant Examiner* — Gwynneth L Howell
(74) *Attorney, Agent, or Firm* — McDonald Hopkins LLC

(57) ABSTRACT

A mask is provided with a mask body part configured to cover a face of a subject, and a cushion member fixed to the mask body part and contacts the face of the subject. The mask body part has an inner side face at least a portion of which faces the face of the subject, an outer side face positioned on an opposite side to the inner side face, and a plurality of protrusion portions provided on the outer side face. The cushion member has a plurality of engagement portions each of which is engaged with a corresponding one of the plurality of protrusion portions.

11 Claims, 9 Drawing Sheets

(56) References Cited

U.S. PATENT DOCUMENTS

| | | | | |
|---|---|---|---|---|
| 2003/0075180 | A1 * | 4/2003 | Raje | A61M 16/0633 128/206.27 |
| 2005/0172969 | A1 | 8/2005 | Ging et al. | |
| 2007/0221227 | A1 | 9/2007 | Ho | |
| 2007/0267023 | A1 | 11/2007 | Ging et al. | |
| 2008/0087287 | A1 | 4/2008 | Ging et al. | |
| 2008/0178886 | A1 | 7/2008 | Lieberman et al. | |
| 2011/0094513 | A1 | 4/2011 | Takatori et al. | |
| 2011/0214674 | A1 | 9/2011 | Ging et al. | |
| 2011/0226240 | A1 | 9/2011 | Navalesi et al. | |
| 2015/0007816 | A1 | 1/2015 | D'Souza et al. | |
| 2015/0099986 | A1 * | 4/2015 | Inoue | A62B 9/006 600/479 |
| 2016/0001028 | A1 | 1/2016 | McAuley et al. | |
| 2016/0175552 | A1 | 6/2016 | Harrington | |
| 2017/0028154 | A1 | 2/2017 | Takatori et al. | |
| 2017/0203068 | A1 | 7/2017 | Ging et al. | |
| 2018/0008848 | A1 * | 1/2018 | Moulton | A41D 13/11 |
| 2018/0228400 | A1 | 8/2018 | Baba et al. | |
| 2020/0269005 | A1 | 8/2020 | Harrington | |
| 2021/0046274 | A1 | 2/2021 | Harrington | |
| 2023/0116907 | A1 | 4/2023 | Harrington | |

FOREIGN PATENT DOCUMENTS

| | | | |
|---|---|---|---|
| JP | 2009-540870 | A | 11/2009 |
| JP | 2010-516411 | A | 5/2010 |
| JP | 2011-115543 | A | 6/2011 |
| JP | 2016530920 | A | 10/2016 |
| JP | 2018-130181 | A | 8/2018 |

OTHER PUBLICATIONS

Extended European Search Report dated Aug. 1, 2022 issued in European Patent Application No. 22 15 9965.7.

Office action issued in Japanese Patent Application No. 2021-040786, dated Jun. 11, 2024.

* cited by examiner

MASK

CROSS-REFERENCE TO RELATED APPLICATIONS

The present application claims priority from Japanese Patent Application No.

2021-040786, filed on Mar. 12, 2021, the entire content of which is incorporated herein by reference.

TECHNICAL FIELD

The presently disclosed subject matter relates to a mask. In particular, the presently disclosed subject matter relates to a medical mask for a mechanical ventilator, that can be worn by a subject.

BACKGROUND ART

A mask disclosed in JP-T-2009-540870 has been, for example, known as a mask used for non-invasive artificial respiration, etc. The respiratory mask for artificial respiration disclosed in JP-T-2009-540870 is provided with a mask shell that is configured to cover a patient's face, and a sealing body that can be put on the user's face and that is formed by an elastic member having flexibility.

By the way, in order to prevent such a situation that air leaks through a gap between the sealing body and the mask shell, the sealing body and the mask shell need to be fixed to each other securely. In this regard, in the respiratory mask disclosed in JP-T-2009-540870, where the sealing body functions as a cushion member and the mask shell functions as a mask body part, a ring member is separately provided in the respiratory mask in order to fix the sealing body and the mask shell to each other. Due to the ring member that needs to be provided separately, the respiratory mask disclosed in JP-T-2009-540870 has a problem that the number of parts of the respiratory mask is increased and the structure of the mask is complicated.

SUMMARY

An object of the presently disclosed subject matter is to provide a mask having a novel structure in view of the foregoing problem. In particular, the object of the presently disclosed subject matter is to provide a mask whose number of parts is reduced and whose structure is simplified.

A mask according to an aspect of the presently disclosed subject matter can include a mask body part configured to cover a face of a subject; and a cushion member fixed to the mask body part and contacts the face of the subject. The mask body part has an inner side face at least a portion of which faces the face of the subject, an outer side face positioned on an opposite side to the inner side face, and a plurality of protrusion portions provided on the outer side face. The cushion member has a plurality of engagement portions each of which is engaged with a corresponding one of the plurality of protrusion portions.

DESCRIPTION OF EMBODIMENT

A mask 1 according to the present embodiment will be described below with reference to the drawings. In description of the present embodiment, a D1 direction, a D2 direction, and a D3 direction may be mentioned appropriately. The D1 to D3 directions are relative directions set in the mask 1 illustrated in FIG. 1. One of the D1 to D3 directions is perpendicular to the other two directions of the D1 to D3 directions.

Figure 1:
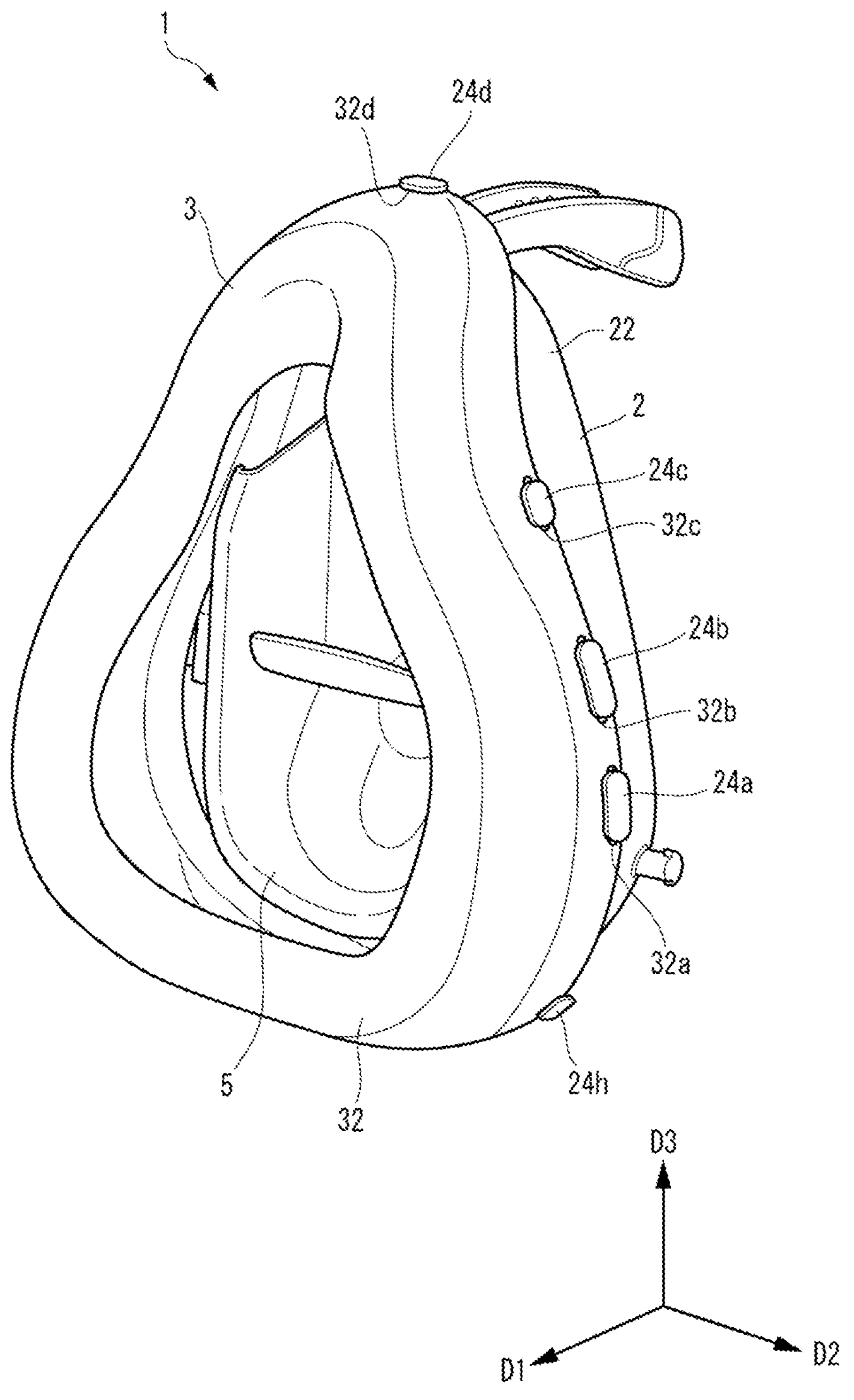
FIG. 1 is a perspective view illustrating the whole of a mask according to an embodiment of the presently disclosed subject matter (which will be hereinafter referred to as the present embodiment).
Figure 2:
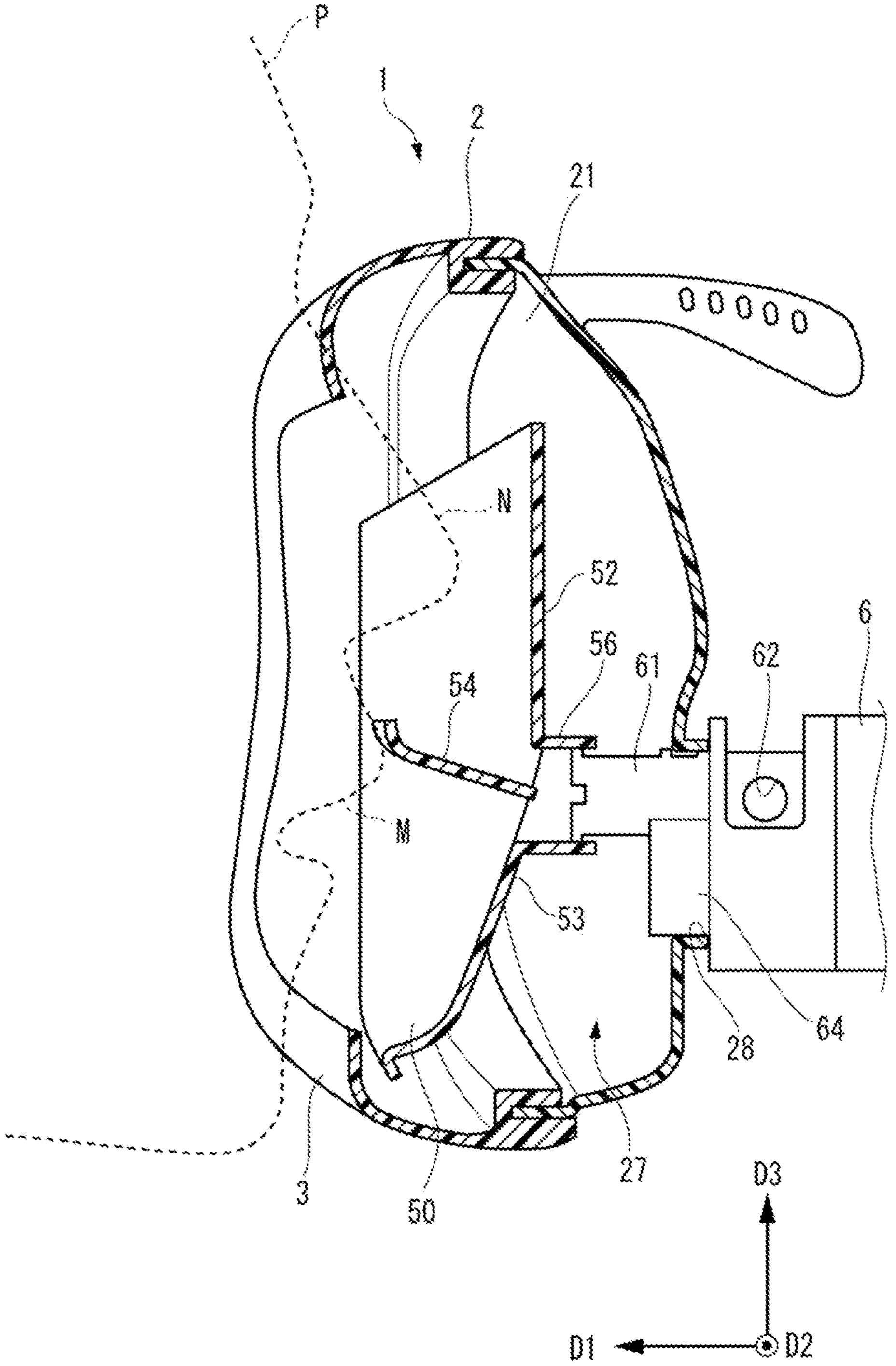
FIG. 2 is a sectional view of the mask according to the present embodiment.

FIG. 1 is a perspective view illustrating the whole of the mask 1 according to the present embodiment. FIG. 2 is a sectional view of the mask 1. As illustrated in FIG. 1 and FIG. 2, the mask 1 is provided with a mask body part 2, a cushion member 3, and an inner cup 5 (an example of an inner part). The mask body part 2 is configured to cover a face of a subject P. The cushion member 3 is fixed to the mask body part 2. The mask 1 is, for example, a medical mask used for non-invasive artificial respiration. In particular, the mask 1 may be a medical mask applied to artificial respiration by CPAP (Continuous Positive Airway Pressure) or NPPV (Noninvasive Positive Pressure Ventilation).

The mask body part 2 is configured to cover parts of the face of the subject P (in particular, a mouth M and a nose N of the subject P). The mask body part 2 is, for example, made of a hard resin such as polycarbonate. The cushion member 3 is configured to contact the face of the subject P when the mask 1 is worn by the subject P. The cushion member 3 is, for example, made of a flexible resin material such as a silicone resin. The inner cup 5 is disposed between the mask body part 2 and the cushion member 3 in the D1 direction. In particular, the inner cup 5 is disposed in an internal space 27 defined by an inner side face 21 of the mask body part 2.

(Configuration of Inner Cup 5)

As illustrated in FIG. 2, the inner cup 5 is configured so that exhaled gas discharged from the mouth M and the nose N of the subject P can be guided toward a joint member 6 that is connected to an exhalation sensor (not illustrated). In this respect, when the inner cup 5 is provided in the mask 1, it is possible to suitably prevent a situation that oxygen gas supplied to the subject P from a not-illustrated oxygen supply pipe through the joint member 6 and the exhaled gas discharged from the subject P are mixed with each other. Therefore, concentration of carbon dioxide contained in the exhaled gas of the subject P can be measured with high accuracy by the exhalation sensor while the oxygen gas is supplied to the subject P from the oxygen supply pipe.

Figure 3:
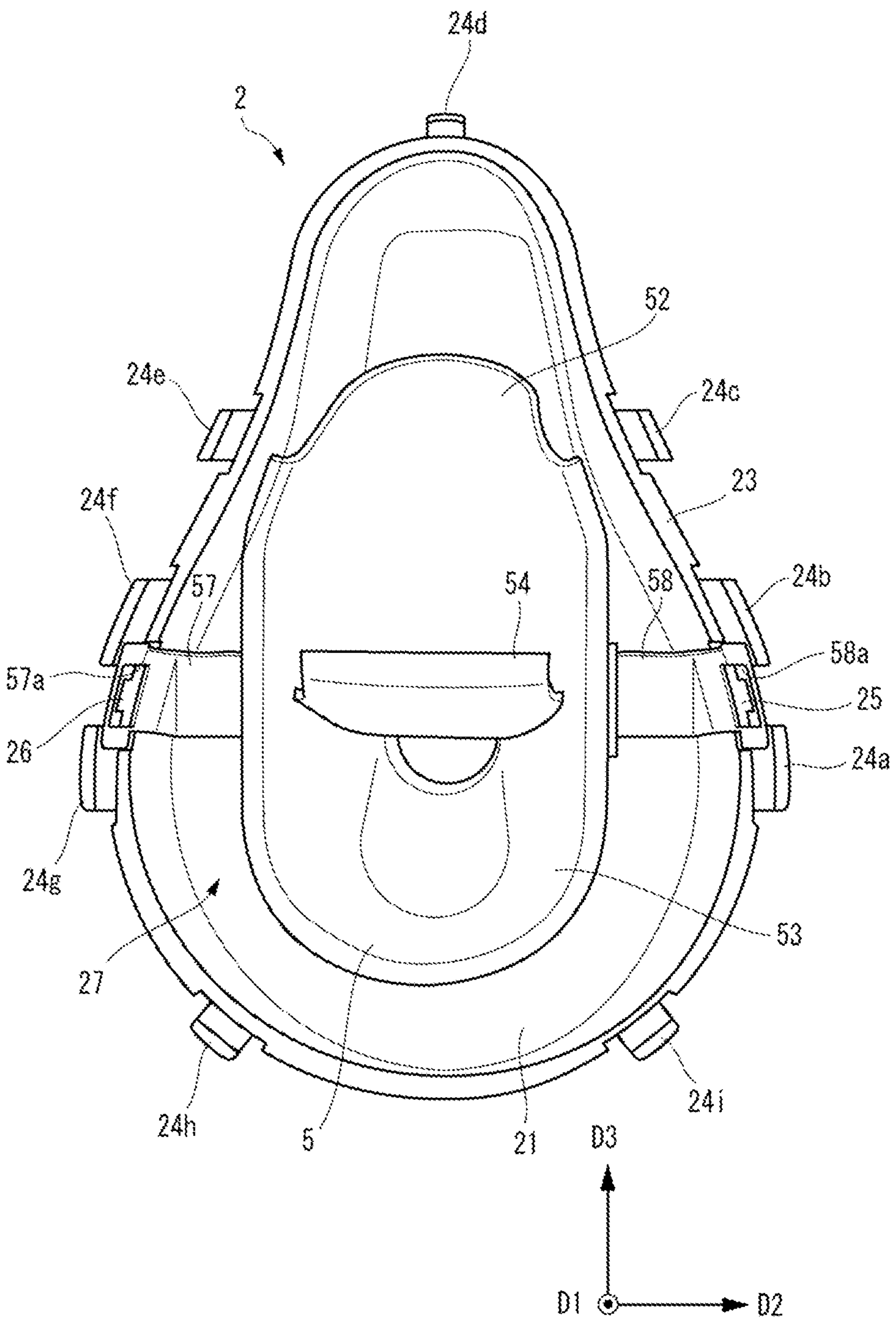
FIG. 3 is a view illustrating an inner side face of a mask body part and an inner cup.

The inner cup 5 is provided with an exhalation collection cup 50 (an example of a cup), and attachment arm portions 57 and 58 (see FIG. 3). The exhalation collection cup 50 is configured to face the mouth M and the nose N of the subject P so that exhaled gas discharged from the mouth M and the nose N can be guided to the exhalation sensor. The exhalation collection cup 50 has an upper side wall portion 52, a lower side wall portion 53, an exhalation guide portion 54, and an exhalation discharge portion 56.

The upper side wall portion 52 is configured to face the nose N of the subject P so that the exhaled gas discharged from the nose N can be guided toward the exhalation discharge portion 56. The lower side wall portion 53 is configured to face the mouth M of the subject P so that the exhaled gas discharged from the mouth M can be guided toward the exhalation discharge portion 56.

The exhalation guide portion 54 is configured to extend from the exhalation discharge portion 56 toward the face of the subject Pin the D1 direction so that the exhaled gas from the nose N and the exhaled gas from the mouth M can be efficiently guided to the exhalation discharge portion 56. The exhalation discharge portion 56 is connected to the upper side wall portion 52 and the lower side wall portion 53. The exhalation discharge portion 56 communicates with an exhaled gas introduction pipe 61 of the joint member 6.

The joint member 6 that has been inserted into an opening portion 28 of the mask body part 2 is fixed to the mask body part 2. The oxygen gas supplied from the oxygen supply pipe is delivered to the internal space 27 of the mask body part 2 through an oxygen gas discharge portion 64 of the joint member 6. The exhalation sensor configured to detect concentration of carbon dioxide of the exhalated gas is disposed to face an exhaled gas outlet 62 of the joint member 6. The exhalation sensor is configured to detect the concentration of the carbon dioxide of the exhaled gas discharged from the exhaled gas outlet 62.

As illustrated in FIG. 3, the attachment arm portions 57 and 58 are configured to connect the exhalation collection cup 50 to the mask body part 2. The attachment arm portions 57 and 58 face each other across the exhalation collection cup 50 in the D2 direction. The attachment arm portion 57 (an example of a first attachment arm portion) is fixed to the exhalation collection cup 50, and extends to a negative side in the D2 direction from one end side of the exhalation collection cup 50. The attachment arm portion 57 has an engagement hole portion 57*a* that is engaged with an engagement attachment portion 26 (an example of a first engagement attachment portion) which will be described later. The engagement hole portion 57*a* is formed as a through hole. The attachment arm portion 58 (an example of a second attachment arm portion) is fixed to the exhalation collection cup 50, and extends to a positive side in the D2 direction from the other end side of the exhalation collection cup 50. The attachment arm portion 58 has an engagement hole portion 58*a* that is engaged with an engagement attachment portion 25 (an example of a second engagement attachment portion) which will be described later. The engagement hole portion 58*a* is formed as a through hole.

(Configuration of Mask Body Part 2)

Figure 4:
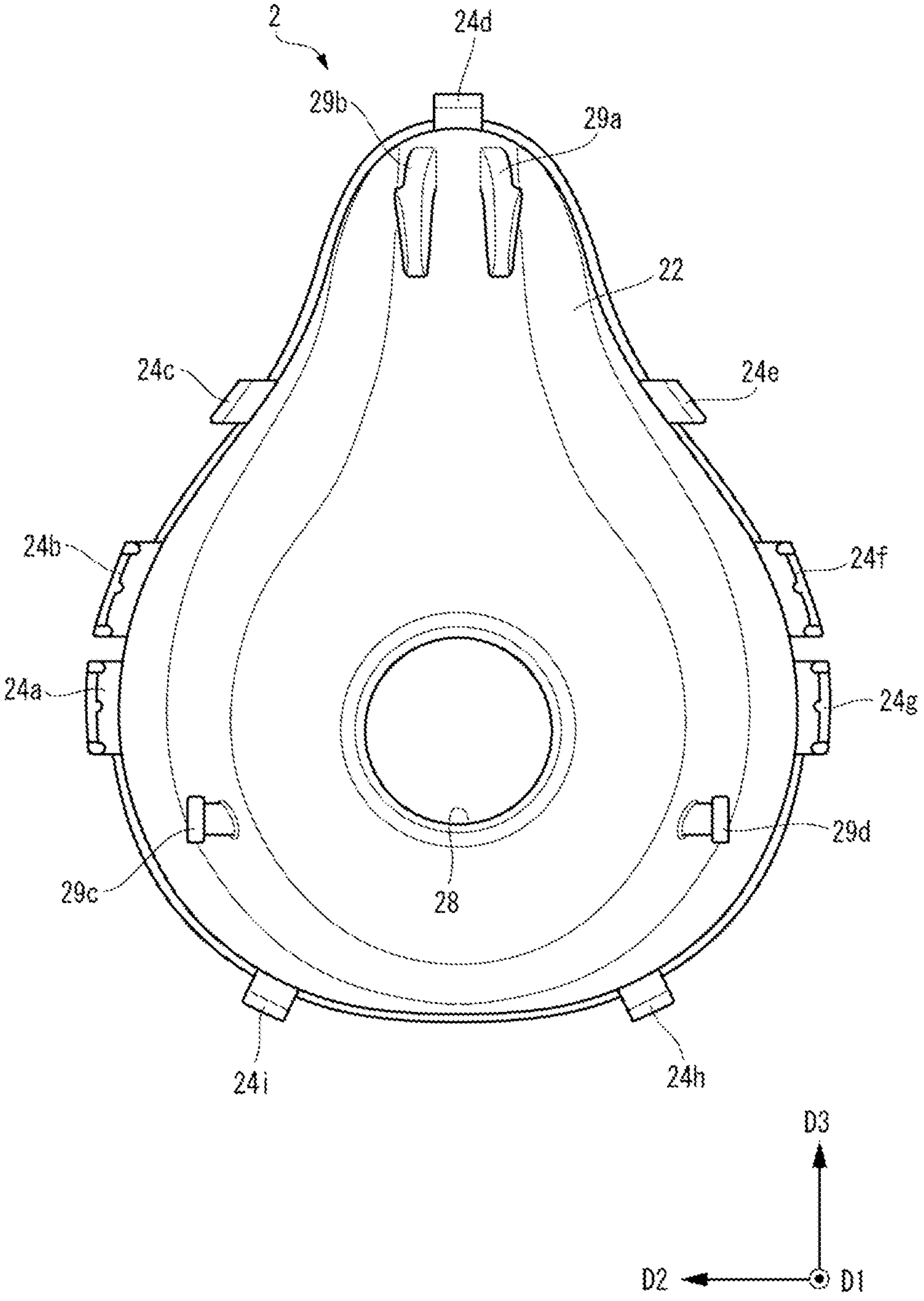
FIG. 4 is a front view illustrating an outer side face of the mask body part.
Figure 5:
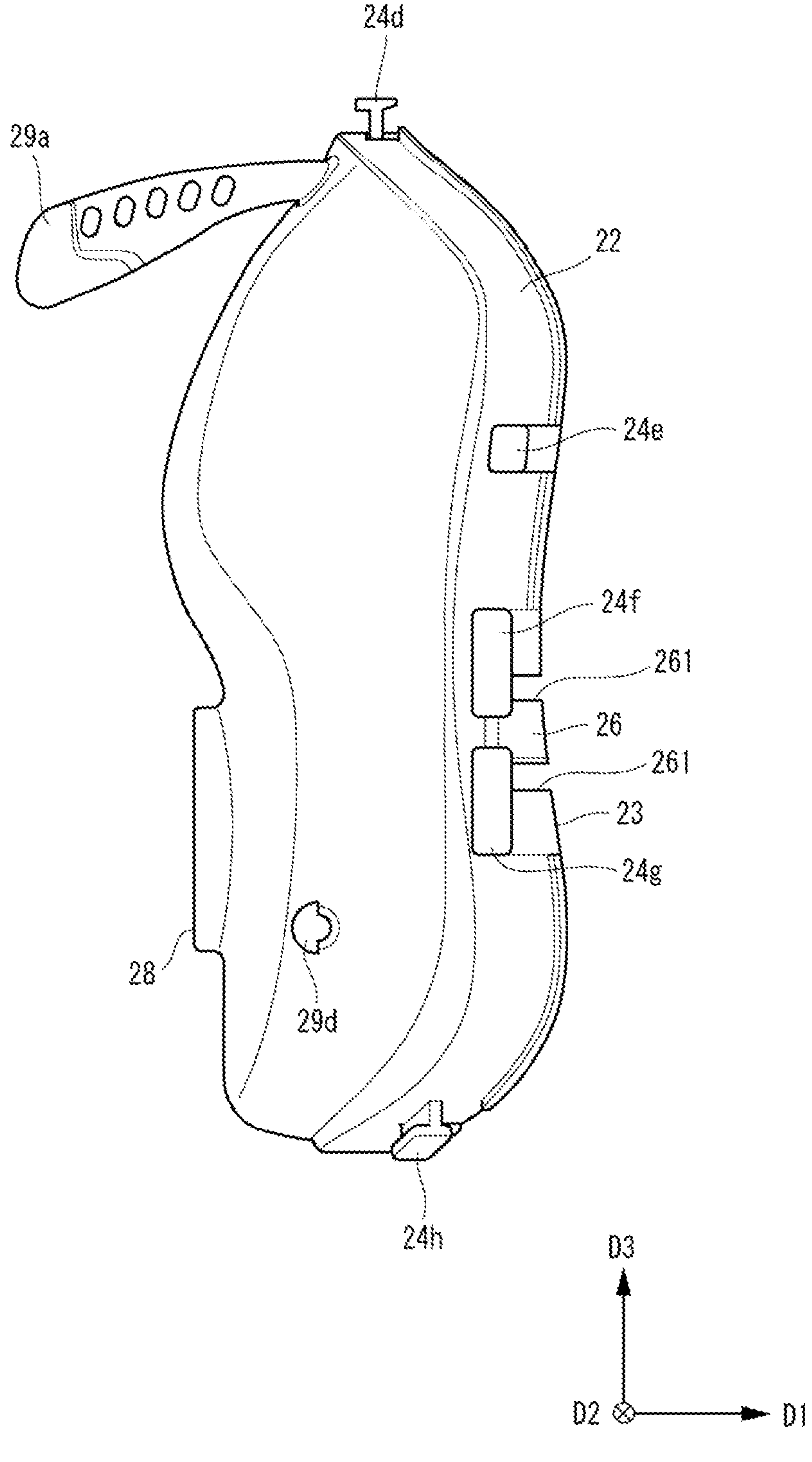
FIG. 5 is a side view illustrating the outer side face of the mask body part.

Next, the configuration of the mask body part 2 will be specifically described with reference to FIGS. 3 to 5. FIG. 3 is a view illustrating the inner side face 21 of the mask body part 2 and the inner cup 5. FIG. 4 is a front view illustrating an outer side face 22 of the mask body part 2. FIG. 5 is a side view illustrating the outer side face 22 of the mask body part 2. As illustrated in FIGS. 3 to 5, the mask body part 2 has the inner side face 21, the outer side face 22, an edge portion 23, a plurality of protrusion portions 24*a* to 24*i*, and the engagement attachment portions 25 and 26. Incidentally, in the following description, the protrusion portions 24*a* to 24*i* may be generically referred to as protrusion portions 24 simply.

The inner side face 21 defines the internal space 27 in which the inner cup 5 is received. In a state in which the mask 1 has been put on the face of the subject, the inner side face 21 partially faces the face of the subject. The outer side face 22 is positioned on an opposite side to the inner side face 21. In the state in which the mask 1 has been put on the face of the subject, the outer side face 22 fronts on the outside. The outer side face 22 partially contacts the cushion member 3 (see FIG. 1). As illustrated in FIG. 4, belt attachment portions 29*a* to 29*d* to which a not-illustrated belt is attached are provided on the outer side face 22. The belt is used to fix the mask 1 to the face of the subject.

The edge portion 23 is positioned at a boundary between the inner side face 21 and the outer side face 22 to be connected to the inner side face 21 and the outer side face 22. The plurality of protrusion portions 24*a* to 24*i* are provided on the outer side face 22. In the present embodiment, the nine protrusion portions 24*a* to 24*i* are provided on the outer side face 22 so as to extend along the edge portion 23, and intermittently surround the edge portion 23. The number of the protrusion portions 24 provided on the outer side face 22 is not particularly limited. The protrusion portion 24*a* faces the protrusion portion 24*g* across the internal space 27. The protrusion portion 24*b* faces the protrusion portion 24*f* across the internal space 27. The protrusion portion 24*c* is opposite to the protrusion portion 24*e* across the internal space 27.

The protrusion portions 24*a* to 24*i* and the belt attachment portions 29*a* to 29*d* are integrally formed with the outer side face 22 of the mask body part 2 by resin molding.

The engagement attachment portion 26 is configured to be engaged with the engagement hole portion 57*a* of the attachment arm portion 57. As illustrated in FIG. 5, the engagement attachment portion 26 is formed in the edge portion 23. In particular, the engagement attachment portion 26 is compartmented and configured by two grooves 261 formed in the edge portion 23. The engagement attachment portion 26 is located between the protrusion portion 24*f* and the protrusion portion 24g that are adjacent to each other in the D3 direction.

A direction in which the engagement attachment portion 26 extends is different from a direction in which each of the protrusion portions 24*f* and 24*g* extends. Specifically, the direction in which the engagement attachment portion 26 extends is substantially orthogonal to the direction in which the protrusion portion 24*f*, 24*g* extends. In this respect, while the engagement attachment portion 26 extends in the D1 direction, the protrusion portion 24*f*, 24*g* extends in the D2 direction.

In a circumferential direction of the edge portion 23, an interval between the protrusion portion 24*f* and the protrusion portion 24*g* is smaller than an interval between the protrusion portion 24*f* and the protrusion portion 24*e* adjacent to the protrusion portion 24*f*, and smaller than an interval between the protrusion portion 24*g* and the protrusion portion 24*h* adjacent to the protrusion portion 24*g*.

In addition, a lengthwise dimension of each of the protrusion portions 24*f* and 24*g* is larger than a lengthwise dimension of each of the protrusion portions 24*e* and 24*h*. Here, in the present embodiment, the lengthwise dimension of the protrusion portion 24 corresponds to a dimension of the protrusion portion 24 in the circumferential direction of the edge portion 23. Moreover, a widthwise dimension of the protrusion portion 24 corresponds to a dimension of the protrusion portion 24 in a direction perpendicular to the circumferential direction of the edge portion 23. A heightwise dimension of the protrusion portion 24 corresponds to a dimension of the protrusion portion 24 in a normal line direction to the outer side face 22 in the vicinity of the protrusion portion 24.

The engagement attachment portion 25 is configured to be engaged with the engagement hole portion 58*a* of the attachment arm portion 58. The engagement attachment portion 25 is formed in the edge portion 23. In particular, the engagement attachment portion 25 is compartmented and configured by two grooves formed in the edge portion 23. The engagement attachment portion 25 is located between the protrusion portion 24*a* and the protrusion portion 24*b*, that are adjacent to each other, in the D3 direction.

The direction in which the engagement attachment portion 25 extends is different from the direction in which each of the protrusion portions 24*a* and 24*b* extends. Specifically, the direction in which the engagement attachment portion 25 extends is substantially orthogonal to the direction in which the protrusion portion 24*a*, 24*b* extends. While the engagement attachment portion 25 extends in the D1 direction, the protrusion portion 24*a*, 24*b* extends in the D2 direction.

In the circumferential direction of the edge portion 23, an interval between the protrusion portion 24*a* and the protrusion portion 24*b* is smaller than an interval between the protrusion portion 24*a* and the protrusion portion 24*i* adjacent to the protrusion portion 24*a*, and smaller than an interval between the protrusion portion 24*b* and the protrusion portion 24*c* adjacent to the protrusion portion 24*b*. In addition, a lengthwise dimension of each of the protrusion portions 24*a* and 24*b* is larger than a lengthwise dimension of each of the protrusion portions 24*c* and 24*i*.

The inner cup 5 is fixed to the mask body part 2 in a state in which the engagement hole portion 57*a* of the attachment arm portion 57 is brought into engagement with the engagement attachment portion 26, and the engagement hole portion 58*a* of the attachment arm portion 58 is brought into engagement with the engagement attachment portion 25. Moreover, since the cushion member 3 is fixed to the mask body part 2 as illustrated in FIG. 1, movement of the inner cup 5 in the D1 direction is completely regulated.

(Configuration of Cushion Member 3)

Figure 6:
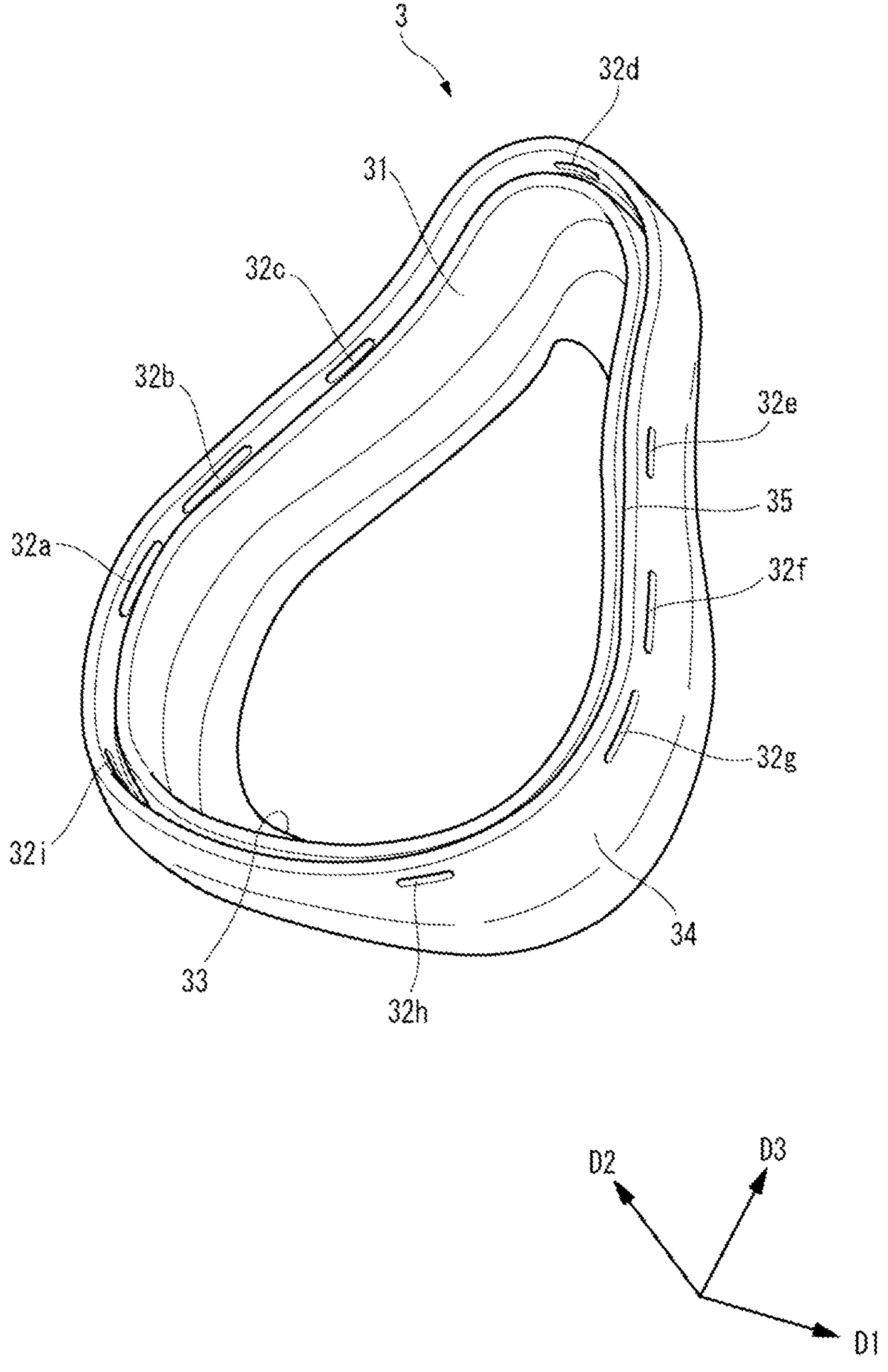
FIG. 6 is a perspective view illustrating a cushion member including a plurality of through holes.

Next, the configuration of the cushion member 3 will be described below with reference to FIG. 6. The cushion member 3 has an outer side face 34 fronting on the outside, an inner side face 31 located on an opposite side to the outer side face 34, and a plurality of elongated through holes 32*a* to 32*i* (an example of engagement portions). Incidentally, in the following description, the through holes 32*a* to 32*i* may be generically referred to as through holes 32 simply.

When the mask 1 is worn by the subject, the outer side face 34 partially contacts the face of the subject. An opening portion 33 is formed in a portion of the outer side face 34 facing the face of the subject. The parts (the mouth and the nose) of the face of the subject face the inner cup 5 through the opening portion 33. The through holes 32*a* to 32*i* penetrate the cushion member 3 so as to extend from the outer side face 34 to the inner side face 31. The nine through holes 32*a* to 32*i* are provided in the outer side face 34 so as to extend along an edge portion 35 of the cushion member 3, and intermittently surround the edge portion 35. A longitudinal direction of each of the elongated through holes 32 is consistent with a circumferential direction of the edge portion 35. The number of the through holes 32 corresponds to the number of the protrusion portions 24.

When the cushion member 3 is fixed to the mask body part 2, each of the protrusion portions 24*a* to 24*i* is engaged with a corresponding one of the through holes 32*a* to 32*i*. For example, the protrusion portion 24*a* is engaged with the through hole 32*a* and the protrusion portion 24*i* is engaged with the through hole 32*i*.

Figure 7A:
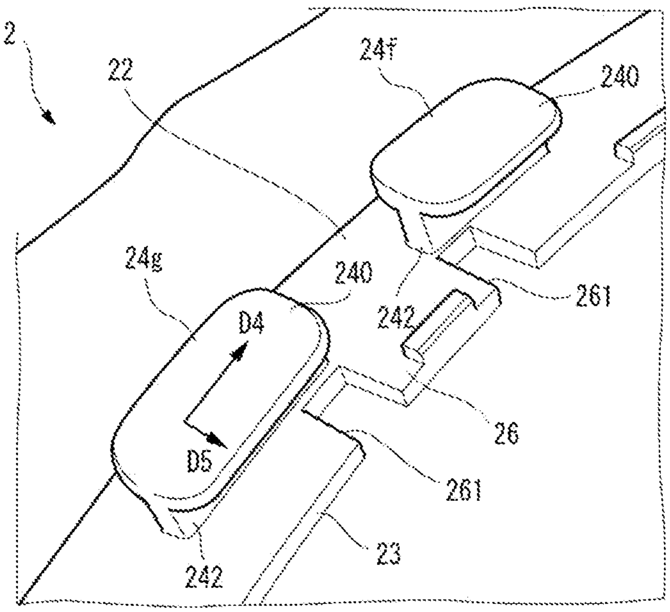
FIG. 7A is an enlarged view illustrating two protrusion portions disposed in the vicinity of an engagement attachment portion in a state in which the cushion member has not been fixed to the mask body part yet.
Figure 7B:
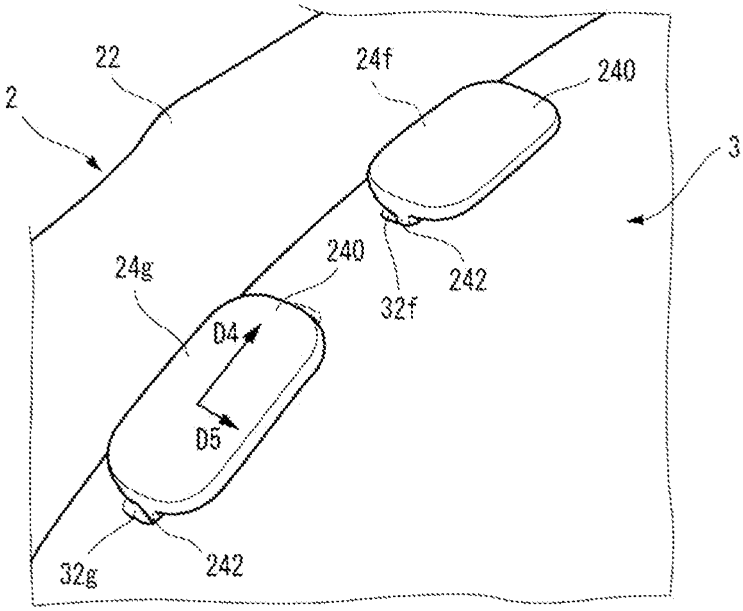
FIG. 7B is an enlarged view illustrating a state in which the two protrusion portions disposed in the vicinity of the engagement attachment portion have been inserted into the through holes formed in the cushion member.

Next, the protrusion portions 24 and the through holes 32 will be described in detail with reference to FIG. 7A and FIG. 7B. FIG. 7A is an enlarged view illustrating the two protrusion portions 24*f* and 24*g* disposed in the vicinity of the engagement attachment portion 26 in a state in which the cushion member 3 has not been fixed to the mask body part 2 yet. FIG. 7B is an enlarged view illustrating a state in which the two protrusion portions 24*f* and 24*g* disposed in the vicinity of the engagement attachment portion 26 have been inserted into the through holes 32*f* and 32*g* formed in the cushion member 3.

As illustrated in FIG. 7A, each of the protrusion portions 24*f* and 24*g* has a standing wall portion 242 protruding from the outer side face 22 of the mask body part 2, and a head portion 240 connected to the standing wall portion 242. Incidentally, each of the nine protrusion portions 24*a* to 24*i* has the standing wall portion 242 and the head portion 240. One end of the standing wall portion 242 is connected to the outer side face 22 and the other end of the standing wall portion 242 is connected to the head portion 240. Each of the protrusion portions 24 is formed into a T shape when viewed from a D4 direction (corresponding to the circumferential direction of the edge portion 23) illustrated in FIG. 7A.

The head portion 240 is substantially formed into a flat face when viewed from a normal line direction of the outer side face 22 in the vicinity of the protrusion portion 24. A dimension (widthwise dimension) of the head portion 240 in a D5 direction is larger than a widthwise dimension of the standing wall portion 242. On the other hand, a dimension (lengthwise dimension) of the head portion 240 in the D4 direction is approximately equal to a lengthwise dimension of the standing wall portion 242.

When the cushion member 3 is fixed to the mask body part 2, the protrusion portion 24*f* is engaged with the through hole 32*f* of the cushion member 3 and the protrusion portion 24*g* is engaged with the through hole 32*g* of the cushion member 3, as illustrated in FIG. 7B. In this state, the cushion member 3 is held between the head portions 240 of the plurality of protrusion portions 24 and the outer side face 22 when the standing wall portions 242 of the plurality of protrusions 24 have been inserted into the plurality of through holes 32 respectively and correspondingly. Thus, the cushion member 3 is fixed to the mask body part 2 by the plurality of head portions 240 and the plurality of standing wall portions 242.

A widthwise dimension of each of the through holes 32 is smaller than the widthwise dimension of each of the head portions 240, but slightly larger than the widthwise dimension of each of the standing wall portions 242. On the other hand, a lengthwise dimension of the through hole 32 is larger than each of the lengthwise dimensions of the head portion 240 and the standing wall portion 242. According to this configuration, the widthwise dimension of the head portion 240 is larger than the widthwise dimension of the through hole 32. Accordingly, the cushion member 3 can be securely held between the head portion 240 and the outer side face 22. Moreover, since the widthwise dimension of the through hole 32 is slightly larger than the widthwise dimension of the standing wall portion 242, the standing wall portion 242 can be easily inserted into the through hole 32 so that a workload for attaching the cushion member 3 to the mask body part 2 can be reduced.

(Effect and Function of Mask 1 According to Present Embodiment)

According to the present embodiment, the plurality of protrusion portions 24*a* to 24*i* provided on the outer side face 22 of the mask body part 2 are respectively and correspondingly engaged with the plurality of through holes 32*a* to 32*i* provided in the cushion member 3, thereby fixing the cushion member 3 to the mask body part 2. Thus, a ring member for fixing the cushion member 3 to the mask body part 2 as in the background-art mask does not need to be separately provided in the mask 1. Consequently, the number of parts of the mask 1 can be reduced and the structure of the mask 1 provided with the inner cup 5 can be simplified.

As another method for fixing the mask body part 2 and the cushion member 3 to each other, a method for fixing the mask body part 2 and the cushion member 3 to each other by an adhesive agent or a method for integrally forming the mask body part 2 and the cushion member 3 by two-color molding can be considered. On the other hand, the fixation method between the mask body part 2 and the cushion member 3 according to the present embodiment can reduce manufacturing cost of the mask 1 provided with the inner cup 5 as compared with these methods.

In addition, the plurality of protrusion portions 24 are provided on the outer side face 22 so as to extend along the edge portion 23 of the mask body part 2. Further, the cushion member 3 is partially held between the plurality of head portions 240 and the outer side face 22 in the state in which the standing wall portions 242 of the plurality of protrusion portions 24 have been inserted into the plurality of through holes 32 respectively and correspondingly. Thus, the cushion member 3 and the mask body part 2 can be fixed to each other securely by the plurality of protrusion portions 24.

Moreover, in the present embodiment, the two engagement attachment portions 25 and 26 are provided not in the outer side face 22 of the mask body part 2 but in the edge portion 23. Therefore, the direction in which the engagement attachment portion 25 extends is substantially orthogonal to the direction in which each of the protrusion portions 24*a* and 24*b* extends, and the direction in which the engagement attachment portion 26 extends is substantially orthogonal to the direction in which each of the protrusion portions 24*f* and 24*f* extends. As a result, a situation in which air leaks out through a gap between the cushion member 3 and the outer side face 22 of the mask body part 2 can be securely prevented in and around an area of the mask body part 2 where the engagement attachment portions 25 and 26 are provided. Thus, high adhesiveness between the cushion member 3 and the mask body part 2 can be ensured over the entire circumference of the edge portion 23 of the mask body part 2.

Further, the interval between the protrusion portion 24*f* and the protrusion portion 24*g* is smaller than the interval between the protrusion portion 24*f* and the protrusion portion 24*e*, and smaller than the interval between the protrusion portion 24*g* and the protrusion portion 24*h*. The lengthwise dimension of each of the protrusion portions 24*f* and 24*g* is larger than the lengthwise dimension of each of the protrusion portions 24*e* and 24*h*. In a similar manner or the same manner, the interval between the protrusion portion 24*a* and the protrusion portion 24*b* is smaller than the interval between the protrusion portion 24*a* and the protrusion portion 24*i* adjacent to the protrusion portion 24*a*, and smaller than the interval between the protrusion portion 24*b* and the protrusion portion 24*c* adjacent to the protrusion portion 24*b*. Further, the lengthwise dimension of each of the protrusion portions 24*a* and 24*b* is larger than the lengthwise dimension of each of the protrusion portions 24*c* and 24*i*.

According to the aforementioned configuration, the fixation between the cushion member 3 and the mask body part 2 can be strengthened in and around the area of the mask body part 2 where the two mounting portions 25 and 26 are provided. As a result, the fixation between the inner cup 5 and the mask body part 2 can be strengthened.

(Mask 1*a* According to Modification of Present Embodiment)

Figure 8:
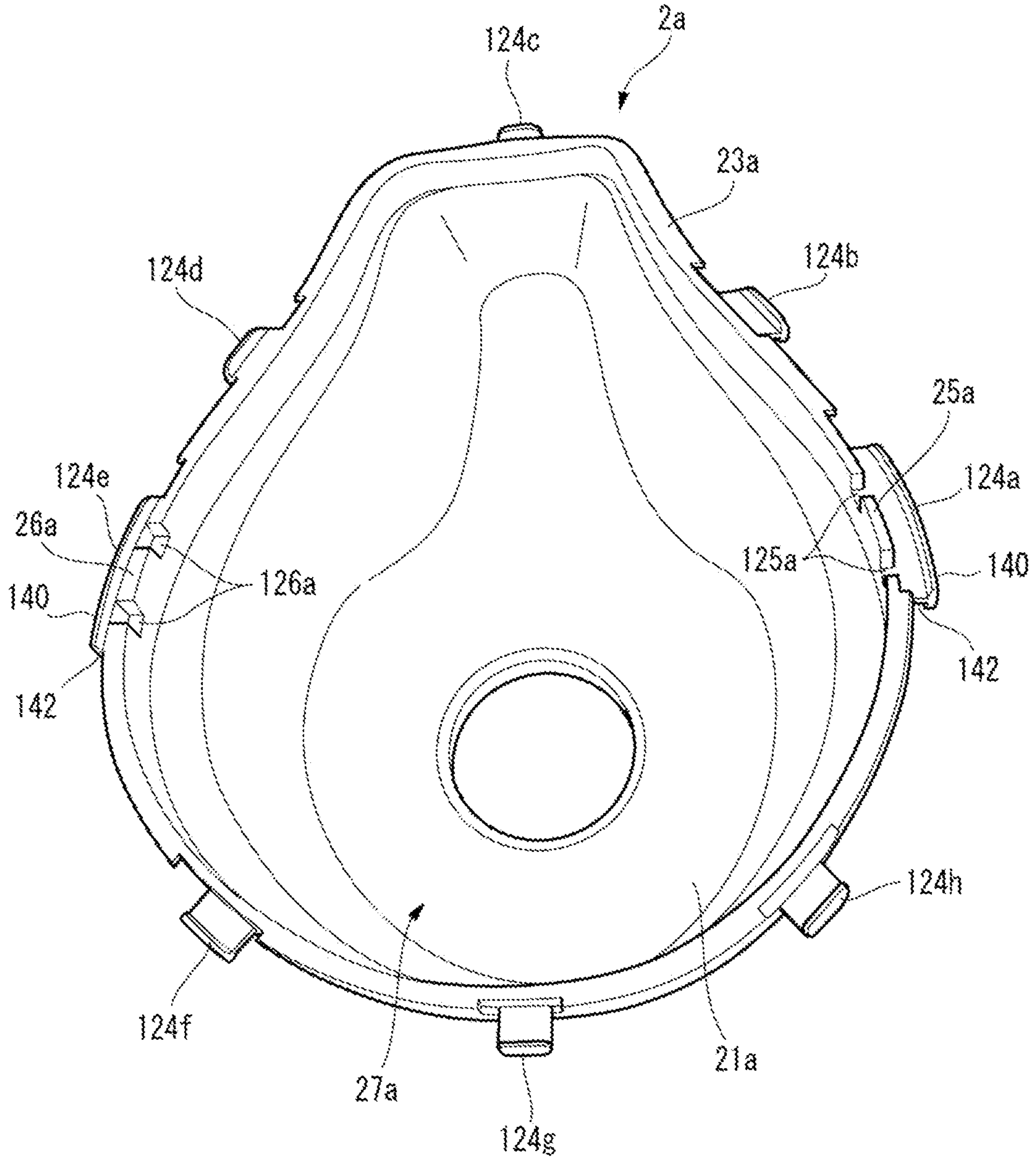
FIG. 8 is a view illustrating a mask body part according to a modification of the present embodiment.
Figure 9:
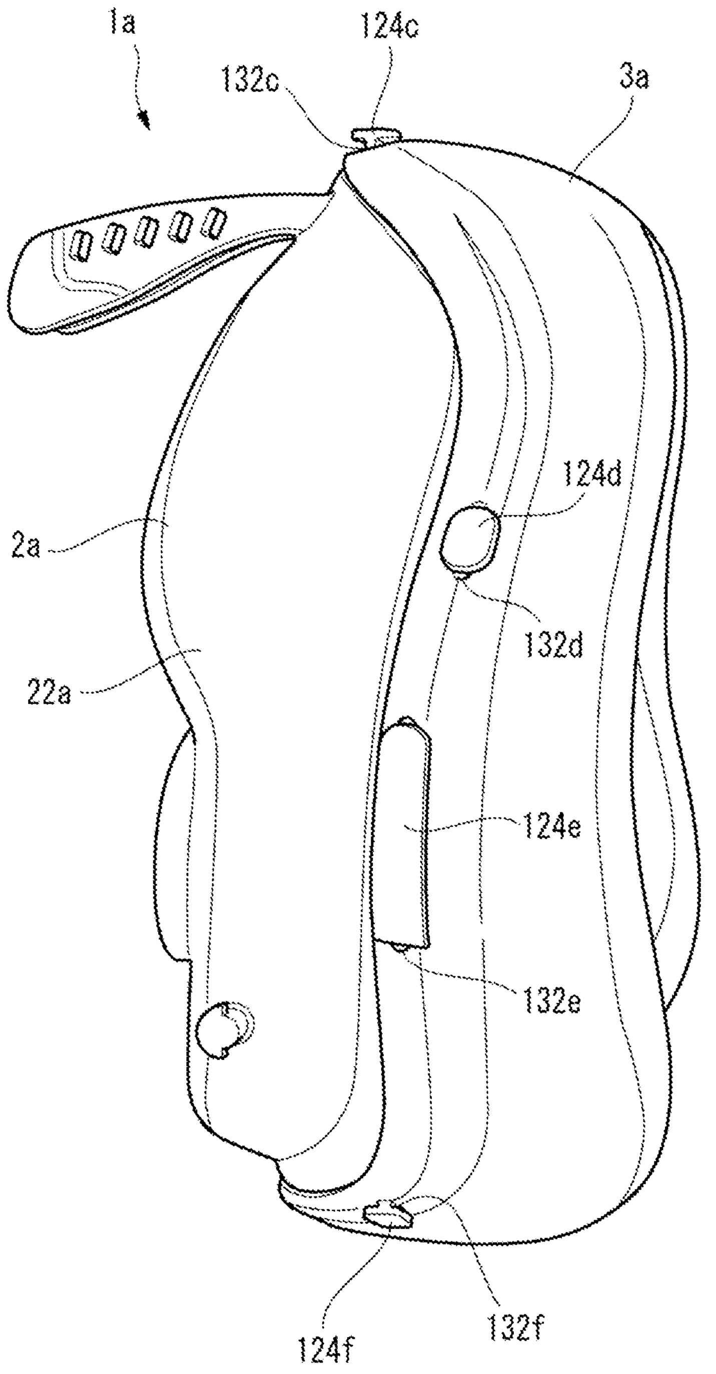
FIG. 9 is a side view illustrating a mask according to the modification of the present embodiment.

Next, a mask 1*a* according to a modification of the present embodiment will be described below with reference to FIG. 8 and FIG. 9. FIG. 8 is a view illustrating a mask body part 2*a* according to the modification of the present embodiment. FIG. 9 is a side view illustrating the mask 1*a* according to the modification of the present embodiment. The mask 1*a* according to the modification differs from the mask 1 according to the present embodiment in configurations of protrusion portions of the mask body part 2*a*. The configurations of the protrusion portions, which are the difference between the present embodiment and the modification, will be mainly described as follows.

As illustrated in FIG. 8 and FIG. 9, the mask body part 2*a* has an inner side face 21*a*, an outer side face 22*a* located on an opposite side to the inner side face 21*a*, an edge portion 23*a* located at a boundary between the inner side face 21*a* and the outer side face 22*a*, and protrusion portions 124*a* to 124*h*. The eight protrusion portions 124*a* to 124*h* are provided on the outer side face 22*a* so as to extend along the edge portion 23*a*, and intermittently surround the edge portion 23*a*. The protrusion portion 124*a* faces the protrusion portion 124*e* across an internal space 27*a* defined by the inner side face 21*a*. Each of the protrusion portions 124*a* to 124*h* has a standing wall portion 142 protruding from the outer side face 22*a*, and a head portion 140 connected to the standing wall portion 142.

Two engagement attachment portions 25*a* and 26*a* are formed in the edge portion 23*a*. The engagement attachment portion 25*a* is compartmented and configured by two grooves 125*a*. The engagement attachment portion 26*a* is compartmented and configured by two grooves 126*a*. The engagement attachment portion 25*a* is engaged with an attachment arm portion 57 of an inner cup 5 illustrated in FIG. 3, and the engagement attachment portion 26*a* is engaged with an attachment arm portion 58.

The protrusion portion 124*a* is provided on the outer side face 22*a* so as to face the engagement attachment portion 25*a*. A dimension (lengthwise dimension) of the protrusion portion 124*a* in a circumferential direction of the edge portion 23*a* is larger than each of lengthwise dimensions of the two protrusion portions 124*b* and 124*h* adjacent to the protrusion portion 124*a*. The protrusion portion 124*e* is provided on the outer side face 22*a* so as to face the engagement attachment portion 26*a*. A lengthwise dimension of the protrusion portion 124*e* is larger than each of length dimensions of the two protrusion portions 124*d* and 124*f* adjacent to the protrusion portion 124*e*. In particular, the lengthwise dimension of the protrusion portion 124*a*, 124*e* may be twice or more as large as the lengthwise dimension of any of the protrusion portions 124*a* to 124*h* other than the protrusion portions 124*a* and 124*e*.

Thus, the mask body part 2*a* according to the modification differs from the mask body part 2 according to the present embodiment in shapes of the protrusion portions formed in the vicinities of the engagement attachment portions. In particular, in the mask body part 2, two protrusion portions are provided on the outer side face in each of the vicinities of the engagement attachment portions. On the other hand, in the mask body part 2*a*, one protrusion portion is provided on the outer side face so as to face each of the engagement attachment portions.

As illustrated in FIG. 9, the mask 1*a* is constituted by the mask body part 2*a*, a cushion member 3*a*, and a not-illustrated inner cup. Each of the protrusion portions 124*a* to 124*h* is engaged with a corresponding one of through holes formed in the cushion member 3*a*, to thereby fix the cushion member 3*a* to the mask body part 2*a*. In this respect, the protrusion portions 124*c* to 124*f* are respectively and correspondingly engaged with through holes 132*c* to 132*f* in a state in which the cushion member 3*a* has been fixed to the mask body part 2*a* in the side view of the mask 1*a* illustrated in FIG. 9.

According to the present modification, the fixation between the cushion member 3*a* and the mask body part 2*a* can be strengthened in and around the area of the mask body part 2*a* where the engagement attachment portion 25*a* is provided and in and around the area of the mask body part 2*a* where the engagement attachment portion 26*a* is provided. As a result, the fixation between the inner cup and the mask body part 2*a* can be strengthened.

Although the embodiment of the present invention has been described above, the technical scope of the present invention should not be exclusively construed based on the description of the embodiments. It is understood by those skilled in the art that the present embodiment is exemplified and various changes can be made on the embodiment within the scope of the invention described in Claims. The technical scope of the present invention should be defined based on the scope of the invention described in Claims and the scopes of equivalents thereto.

In the present embodiment, the through holes 32 engaged with the protrusion portions 24 of the mask body part 2 are formed along the edge portion of the cushion member 3. However, a plurality of bottomed grooves may be formed along the edge portion of the cushion member 3 in place of the through holes. Even in such a case, the cushion member 3 and the mask body part 2 can be fixed to each other when the plurality of bottomed grooves of the cushion member 3 are engaged with the plurality of protrusion portions 24 respectively and correspondingly.

Moreover, in the present embodiment, the engagement hole portions 57*a* and 58*a* provided in the attachment arm portions 57 and 58 are formed as through holes, but may be formed as bottomed grooves in place of the through holes.

Further, each of the engagement attachment portions 25 and 26 formed in the edge portion 23 is formed by the two grooves so as to extend in the D1 direction. However, the present embodiment is not limited thereto. For example, the engagement attachment portion 25, 26 may be formed as a protrusion portion protruding in the D2 direction from the inner side face 21 of the mask body part 2. Also in this case, the inner cup 5 can be fixed to the mask body part 2 when the engagement hole portions 57*a* and 58*a* formed as the through holes or the bottomed grooves are engaged with the engagement attachment portions 25 and 26 formed as the protrusion portions in a similar manner or the same manner.

Moreover, in the present embodiment, the widthwise dimension of the head portion 240 is larger than the widthwise dimension of the standing wall portion 242, but the lengthwise dimension of the head portion 240 is approximately equal to the lengthwise dimension of the standing wall portion 242, as illustrated in FIG. 7A. However, the present embodiment is not limited thereto. For example, the lengthwise dimension of the head portion 240 may be larger than the lengthwise dimension of the standing wall portion 242, but the widthwise dimension of the head portion 240 may be approximately equal to the widthwise dimension of the vertical wall portion 242. Alternatively, the lengthwise dimension of the head portion 240 may be larger than the lengthwise dimension of the standing wall portion 242, and the widthwise dimension of the head portion 240 may be larger than the widthwise dimension of the standing wall portion 242.

In addition, the inner cup 5 is received in the internal space 27 of the mask body part 2 in the present embodiment. However, the mask 1 may not be provided with the inner cup 5. Moreover, another inner member in place of the inner cup 5 may be received in the internal space 27.

According to the aforementioned configuration, each of the plurality of protrusion portions provided on the outer side face of the mask body part is engaged with one of the plurality of engagement portions, so that the cushion member is fixed to the mask body part. Thus, a ring member for fixing the cushion member and the mask body part to each other as in a background-art mask does not have to be separately provided in the mask, so that the number of parts of the mask can be reduced and the structure of the mask can be simplified.

According to the presently disclosed subject matter, it is possible to provide a mask whose number of parts is reduced and whose structure is simplified.

What is claimed is:

1. A mask comprising:
- a mask body part configured to cover a face of a subject; and
- a cushion member fixed to the mask body part and is configured to contact the face of the subject,
- wherein the mask body part has:
  - an inner side face at least a portion of which is configured to face the face of the subject,
  - an outer side face positioned on an opposite side to the inner side face, and
  - a plurality of protrusions provided on the outer side face;
- wherein the cushion member has a plurality of through holes each of which is engaged with a corresponding one of the plurality of protrusions, and an inner part disposed between the mask body part and the cushion member,
- wherein the inner part has a cup configured to face at least one of a nose and a mouth of the subject, and an attachment arm configured to connect the cup to the mask body part,
- wherein the mask body part further has an engagement attachment portion engaged with the attachment arm,
- wherein the mask body part further has an edge portion located between the inner side face and the outer side face, and connected to the inner side face and the outer side face,
- wherein the engagement attachment portion is provided in the edge portion of the mask body part,
- wherein the engagement attachment portion is a wall formed between two grooves formed in the edge portion, and wherein a direction in which the wall extends is different from a direction in which each of the protrusions extends.

2. The mask according to claim 1, wherein the mask body part further has an edge portion located between the inner side face and the outer side face, and connected to the inner side face and the outer side face;

the plurality of protrusions are provided on the outer side face so as to extend along the edge portion of the mask body part; and the plurality of through holes are provided along an edge portion of the cushion member.

3. The mask according to claim 1, wherein each of the protrusions has:

a standing wall portion that protrudes from the outer side face, and a head portion connected to the standing wall portion;

one end of a respective standing wall portion is connected to the outer side face, and an other end of the respective standing wall portion is connected to a respective head portion; and the cushion member is held between the head portion and the outer side face in a state where the standing wall portions of the protrusions have been inserted into the through holes respectively and correspondingly.

4. The mask according to claim 3, wherein a widthwise dimension of the head portion is larger than a widthwise dimension of the respective standing wall portion, or a lengthwise dimension of the head portion is larger than a lengthwise dimension of the respective standing wall portion.

5. The mask according to claim 1, wherein the direction in which the grooves extend is substantially orthogonal to the direction in which each of the protrusions extends.

6. The mask according to claim 1, wherein the plurality of the protrusions face each other across an internal space of the mask body part defined by the inner side face.

7. The mask according to claim 1, wherein an interval between a first protrusion and a second protrusion is smaller than an interval between the first protrusion and another protrusion adjacent to the first protrusion.

8. The mask according to claim 7, wherein each of lengthwise dimensions of the first protrusion and the second protrusion is larger than a lengthwise dimension of the other protrusion.

9. The mask according to claim 1, wherein the attachment arm has a first attachment arm, and a second attachment arm that faces the first attachment arm;

the engagement attachment portion comprises a first engagement attachment portion engaged with the first attachment arm, and a second engagement attachment portion engaged with the second attachment arm;

a first groove of the two grooves is located between, of the protrusions, a first protrusion and a second protrusion that are adjacent to each other;

a second groove of the two grooves is located between, of the protrusions, a third protrusion and a fourth protrusion that are adjacent to each other;

the first protrusion and the third protrusion face each other across an internal space of the mask body part defined by the inner side face; and the second protrusion and the fourth protrusion face each other across the internal space.

10. The mask according to claim 1, wherein the attachment arm has a first attachment arm, and a second attachment arm that faces the first attachment arm;

the groove has a first groove engaged with the first attachment arm, and a second groove engaged with the second attachment arm;

the first groove faces the first protrusion of the protrusions;

the second groove faces the second protrusion of the protrusions;

the first protrusion of the protrusions and the second protrusion of the protrusions face each other across an internal space of the mask body part defined by the inner side face;

a lengthwise dimension of the first protrusion is larger than a lengthwise dimension of another protrusion adjacent to the first protrusion; and a lengthwise dimension of the second protrusion is larger than a lengthwise dimension of another protrusion adjacent to the second protrusion.

11. The mask according to claim 1, wherein the engagement attachment portion is formed between the plurality of protrusions.

* * * * *